United States Patent [19]

Nakamura

[11] Patent Number: 4,996,975
[45] Date of Patent: Mar. 5, 1991

[54] ELECTRONIC ENDOSCOPE APPARATUS CAPABLE OF WARNING LIFETIME OF ELECTRONIC SCOPE

[75] Inventor: Toru Nakamura, Tochigi, Japan

[73] Assignee: Kabushiki Kaisha Toshiba, Kawasaki, Japan

[21] Appl. No.: 531,391

[22] Filed: Jun. 1, 1990

[30] Foreign Application Priority Data

Jun. 1, 1989 [JP] Japan ................................. 1-137453

[51] Int. Cl.⁵ ............................................... A61B 1/00
[52] U.S. Cl. ........................................... 128/6; 128/4; 358/98
[58] Field of Search .......................... 128/4, 6; 358/98

[56] References Cited

U.S. PATENT DOCUMENTS

| Re. 32,421 | 5/1987 | Hattori ..................................... 128/6 |
| 4,841,363 | 6/1989 | Ams et al. ............................... 358/98 |
| 4,865,018 | 9/1989 | Kanno et al. ........................... 128/6 |
| 4,905,668 | 3/1990 | Ohsawa ................................... 128/6 |
| 4,916,533 | 4/1990 | Gillies et al. ........................... 358/98 |
| 4,920,413 | 4/1990 | Nakamura et al. ..................... 358/98 |

*Primary Examiner*—William H. Grieb
*Attorney, Agent, or Firm*—Foley & Lardner, Schwartz, Jeffery, Schwaab, Mack, Blumenthal & Evans

[57] ABSTRACT

In an electronic endoscope apparatus, comprising: there are provided an electronic scope having an image sensor at a distal end thereof and an angle operation portion adjacent to the image sensor; a scope unit coupled with the electronic scope, including an endoscopic operation switch mechanically connected to the electronic scope, a scope computer for processing a switch operation signal derived from the endoscopic operation switch so as to obtain first use-history data on the operation switch, and a memory device for temporarily storing the first use-history data therein; and, a main unit including a signal processor for processing an image signal derived from the image sensor so as to produce an endoscopic image signal of a biological body under medical examination, a system computer for fetching the use-history data on the operation switch from the memory device via the scope computer, and a display unit for selectively displaying an endoscopic image of the biological body in response to the endoscopic image signal and use-history information in response to the fetched used-history data.

20 Claims, 12 Drawing Sheets

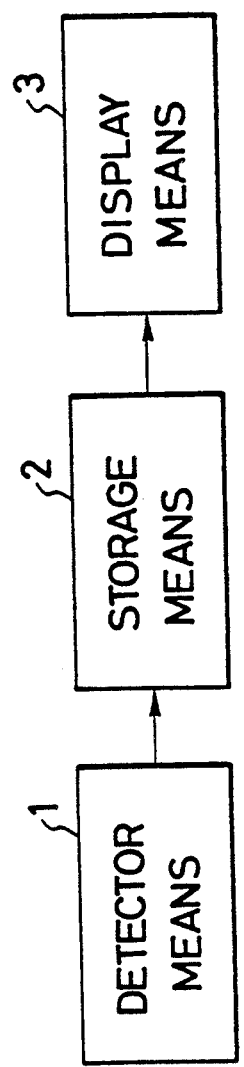
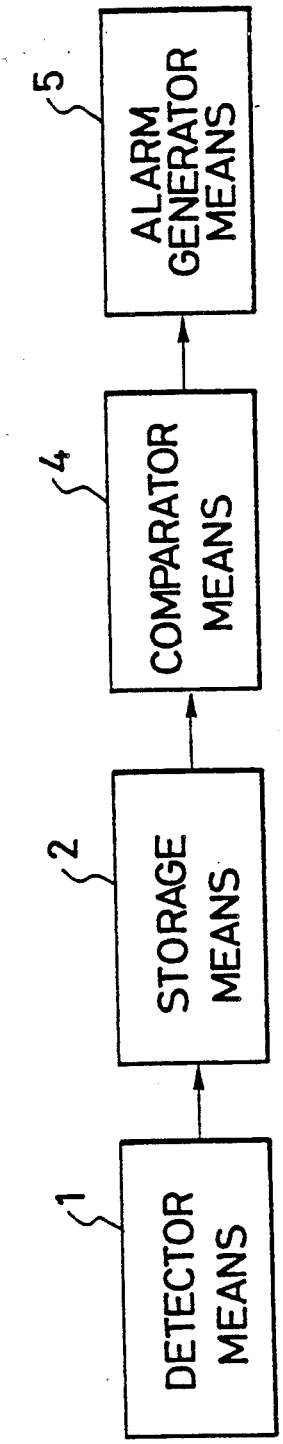

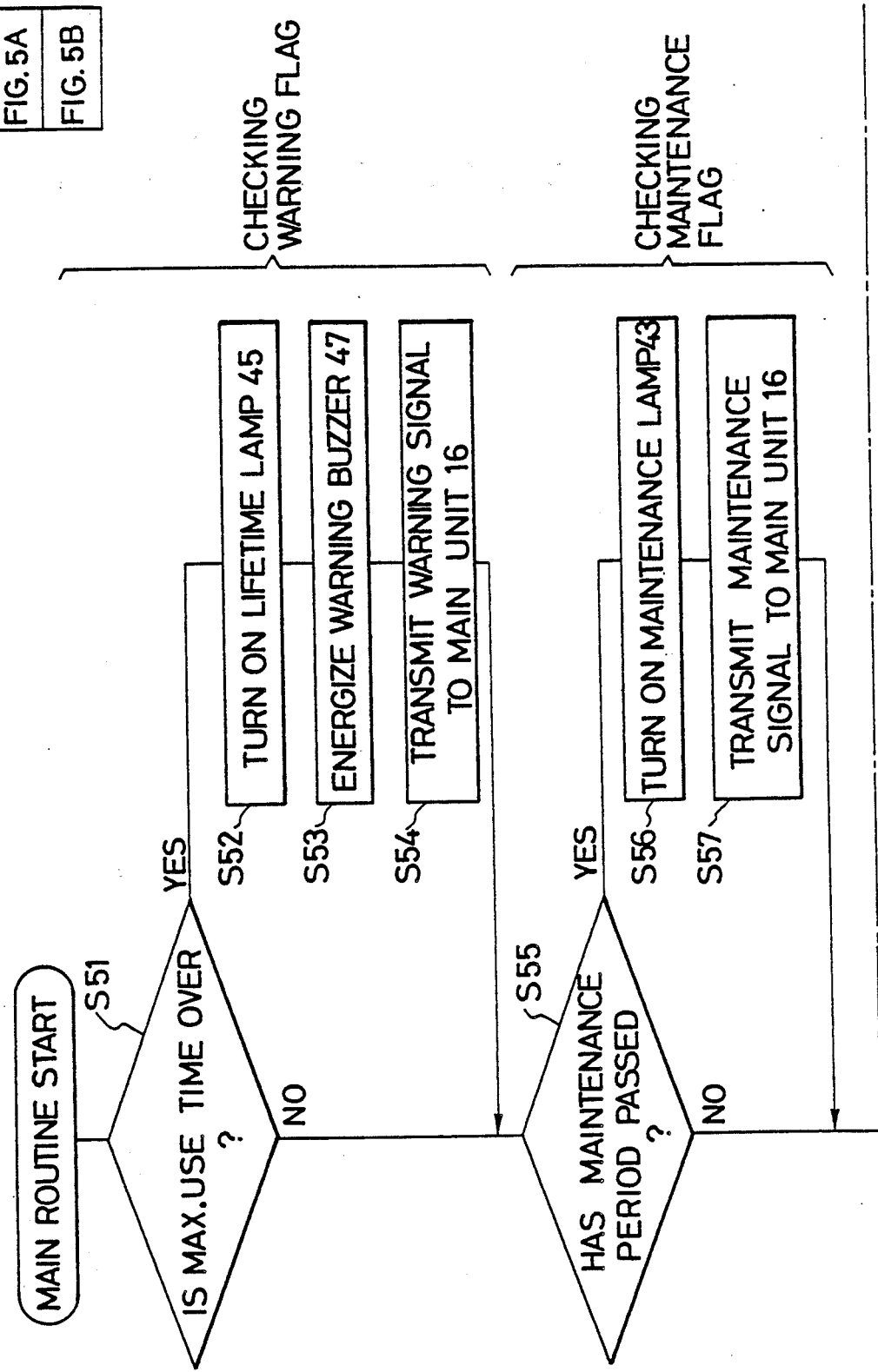

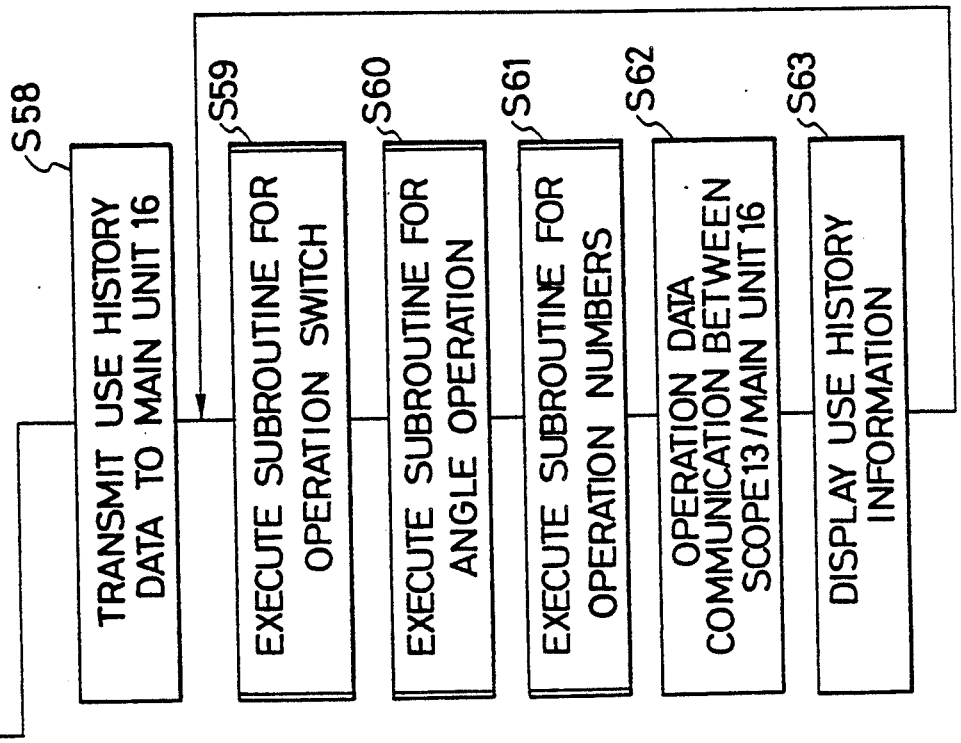

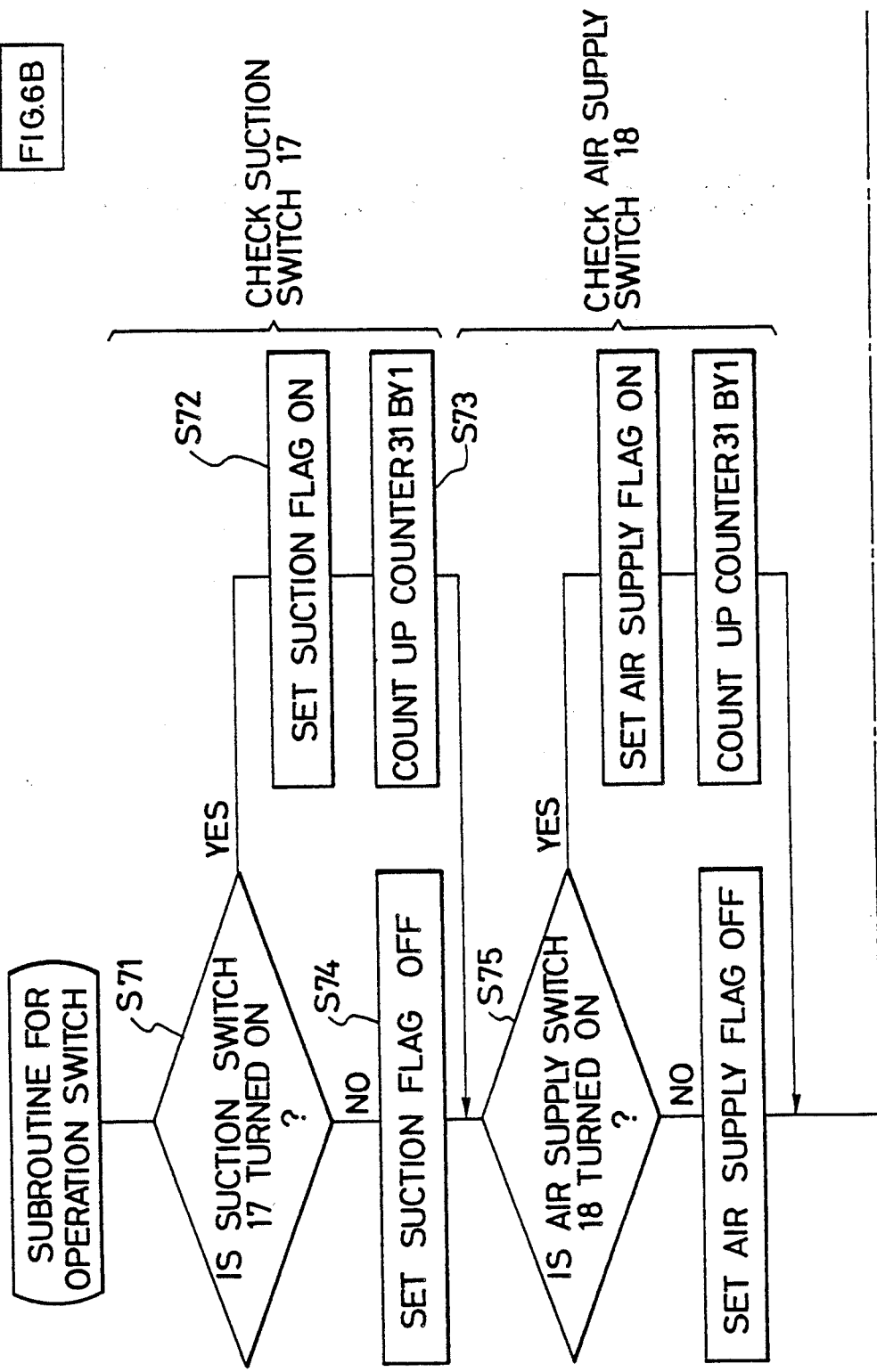

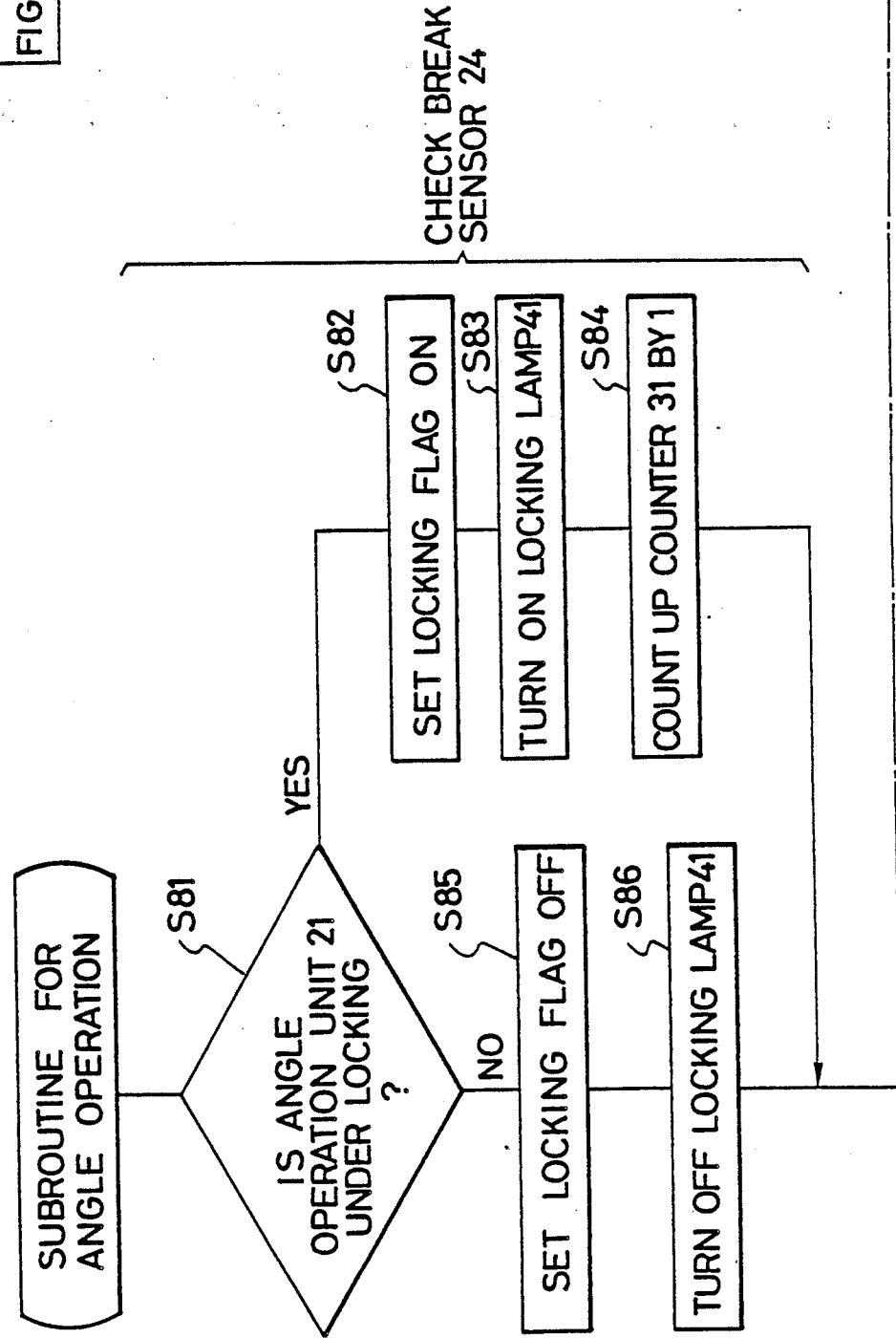

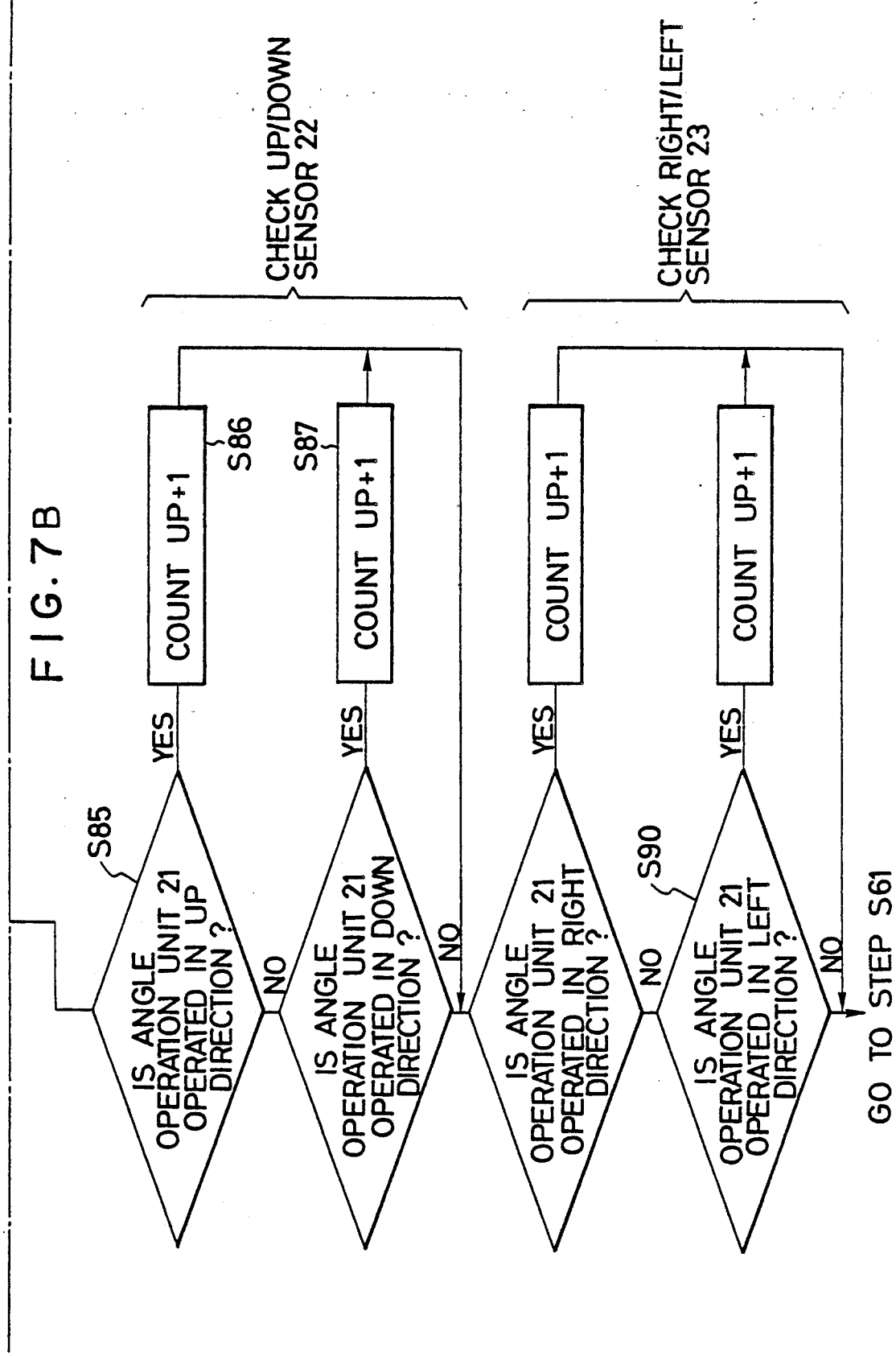

4,996,975

ELECTRONIC ENDOSCOPE APPARATUS CAPABLE OF WARNING LIFETIME OF ELECTRONIC SCOPE

BACKGROUND OF THE INVENTION

1. Field of the Invention

The present invention relates to an electronic endoscope apparatus capable of automatically warning lifetimes of various components employed in an electronic scope.

2. Description of the Related Art

In a field of the recent endoscope apparatuses, there exist two typical sorts: a fiber scope type endoscope apparatus and an electronic endoscope apparatus. Both types of endoscope apparatuses employ various operation switches to achieve various functions required for easily, smoothly observing a body cavity of a biological body under medical examination.

More specifically, there are provided an angle operation unit (knob) for adjusting a curvature of a curved (angle) portion of a scope insertion unit which is inserted into a body cavity; an air supply switch for supplying air through this insertion unit to a distal end of the fiber scope or electronic scope; a water supply switch; an air suction switch and so on.

In the above-described fiber scope type endoscope apparatus, the normal endoscopic operation and observation can be achieved unless these operation switches are brought into malfunctions and the optical fibers are mechanically broken due to an excessive bending force. That is, when the optical fibers are broken, some pixel damages appear in the observed image, which implies that use of the optical fibers reaches the lifetime thereof.

In the other type of electronic endoscope apparatus employing the electronic scope instead of such an optical fiber, the above-described observation checking method is no longer utilized. Therefore, use history information such as a use time period and a manual operation number is manually recorded by an endoscope user so as to grasp necessities of a periodic maintenance and of subsitution due to a lifetime, or malfunction.

Under such circumstances, there are problems in the conventional electronic endoscope apparatuses. That is, the manual use-history recording work may give excessive workload to any endoscope operators and also may induce inaccurate use-history data. In the worst case, a very serious accident may occur if the incorrect use-history record is made, or the components of the electronic scope unit are overused after their lifetimes.

SUMMARY OF THE INVENTION

The present invention has been made in an attempt to solve the above-described problems of the conventional electronic endoscope apparatus, and therefore has an object to provide an electronic endoscope apparatus capable of automatically acquiring use-history data of an electronic scope without any manual use-history recording workload.

An electronic endoscope apparatus, according to the present invention, comprises:

an electronic scope having an image sensor (1) at a distal end thereof and an angle operation portion adjacent to the image sensor (1);

a scope unit (13) coupled with the electronic scope, including an endoscopic operation switch (17:20) mechanically connected to the electronic scope, a scope computer (25) for processing a switch operation signal derived from the endoscopic operation switch (17:20) so as to obtain first use-history data on the operation switch (17:20), and a memory device (29) for temporarily storing the first use-history data therein; and, a main unit (16) including a signal processor (14) for processing an image signal derived from the image sensor (11) so as to produce an endoscopic image signal of a biological body under medical examination, a system computer (26) for fetching the use-history data on the operation switch from the memory device (29) via the scope computer (25), and a display unit (15) for selectively displaying an endoscopic image of the biological body in response to the endoscopic image signal and use-history information in response to the fetched used-history data.

Furthermore, in accordance with the present invention, an electronic endoscope assembly (200) comprises:

an electronic scope having an image sensor (1) at one end thereof and an angle operation portion adjacent to the image sensor (1);

an image driver unit (240) for driving the image sensor (1) to produce an endoscopic image signal of a biological body under medical examination; and, a scope control unit (220) connected to the other end of the electronic scope, including a scope computer (25) for processing a switch operation signal derived from an endoscope operation switch (17:20) mechanically connected to the electronic scope so as to obtain first use-history data on the operation switch (17:20), and a memory device (29) for temporarily storing the first use-history data for a use-history condition displaying purpose.

BRIEF DESCRIPTION OF THE DRAWINGS

For a better understanding of the present invention, reference is made to the following descriptions in conjunction with the accompanying drawings, in which:

FIGS. 1 and 2 represent basic ideas of the present invention;

FIGS. 5a and 5b are a flowchart for explaining a main routine of the operations performed in the first electronic endoscope apparatus shown in FIG. 3;

FIGS. 6a, 6b, 7a, 7i b and 8a and 8b are flowcharts for explaining subroutines of the various checking operations executed in the first electronic endoscope apparatus represented in FIG. 3; and, FIG. 9 is a partially exploded view of an electronic endoscope assembly according to a second preferred embodiment of the present invention.

DETAILED DESCRIPTION OF THE PREFERRED EMBODIMENTS

Basic Ideas

Figure 3:
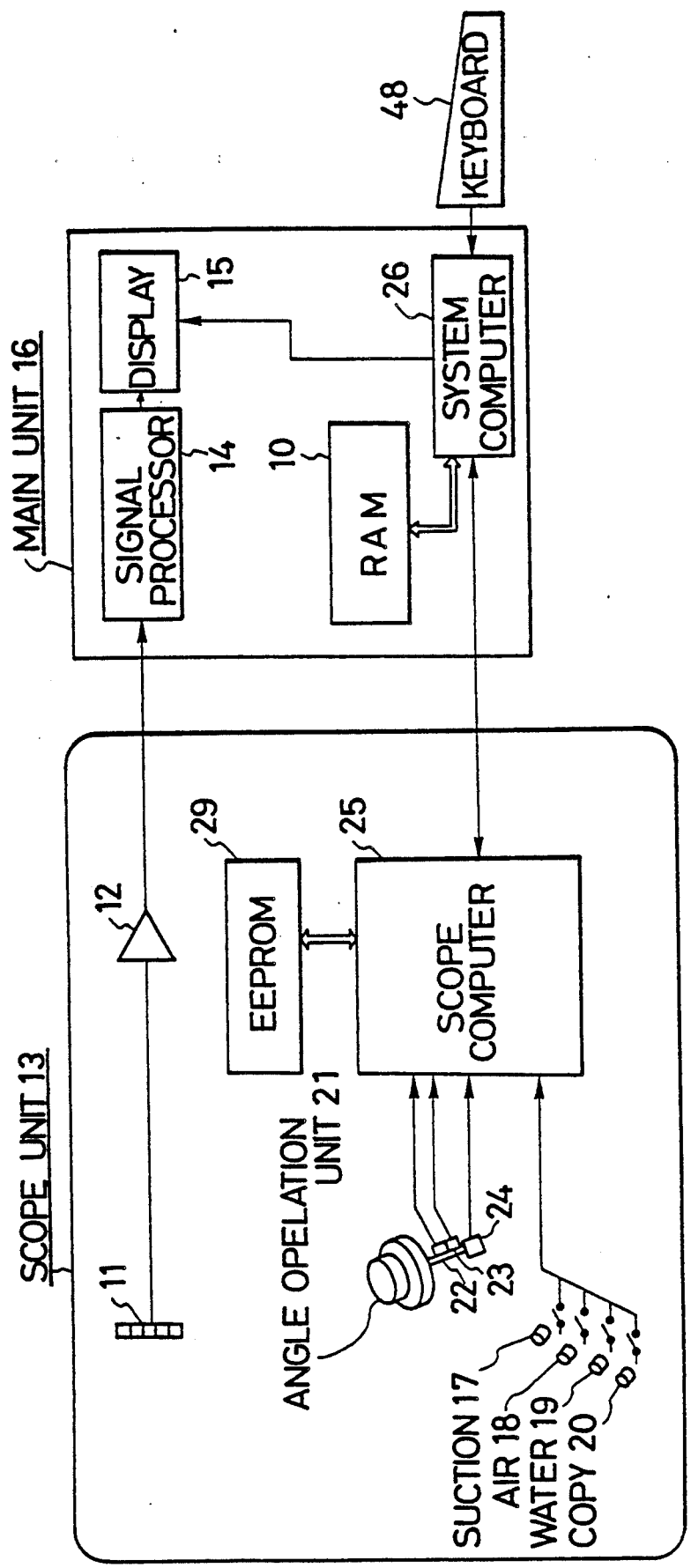
FIG. 3 is a schematic block diagram of an arrangement of an electronic endoscope apparatus according to a first preferred embodiment of the present invention.

In FIG. 1, there is shown a first basic idea of an electronic endoscope apparatus according to the present invention.

This electronic endoscope apparatus is constructed of: detector means 1 for detecting the number of use, or an operating time period of various endoscope members employed in an electronic scope to output operation data of the various endoscope members; storage means 2 for firstly accumulating the operation data of the endoscope members and for secondly storing therein the accumulated data as use-history data thereof; and display means 3 for displaying the use-history data of the endoscope members read out from the storage means 1.

Thus, there are particular advantages of the first basic idea as follows:

For instance, data on use numbers of a water supply switch is detected from the detector means 1, and this operation data of the water supply switch is accumulated so as to obtain use-history data thereof; and then the use-history data is stored in the storage means 2. When the use-history data is displayed on the display means 3, the malfunction of the electronic endoscope can be prevented without loading a cumbersome history recording workload on an operator, since he can judge the lifetime of the electronic endoscope by considering such historical information.

FIG. 2 illustrates a second basic idea of an electronic endoscope apparatus according to the present invention.

As apparent from FIG. 2, the use-history data on the various endoscope members are similarly stored in the storage means 2. In comparator means 4, allowable use data, e.g., an allowable lifetime has been previously set and is compared with the use-history data read out from the storage mean 2. When the detected use-history data exceeds over the allowable lifetime, an alarm signal is supplied from this comparator means 4 to alarm generator means 5. Accordingly, the alarm or warning is produced from this alarm generator means 5.

In accordance with the second basic idea, when an alarm is made from the alarm generator means 5 by judging that the detected use-history data exceeds over the preset allowable lifetime, an operator can firmly, readily recognize a time required for a periodic maintenance and/or a lifetime of an electronic scope employed in the electronic endoscope apparatus according to the present invention.

Arrangement of First Electronic Endoscope Apparatus

Figure 4:
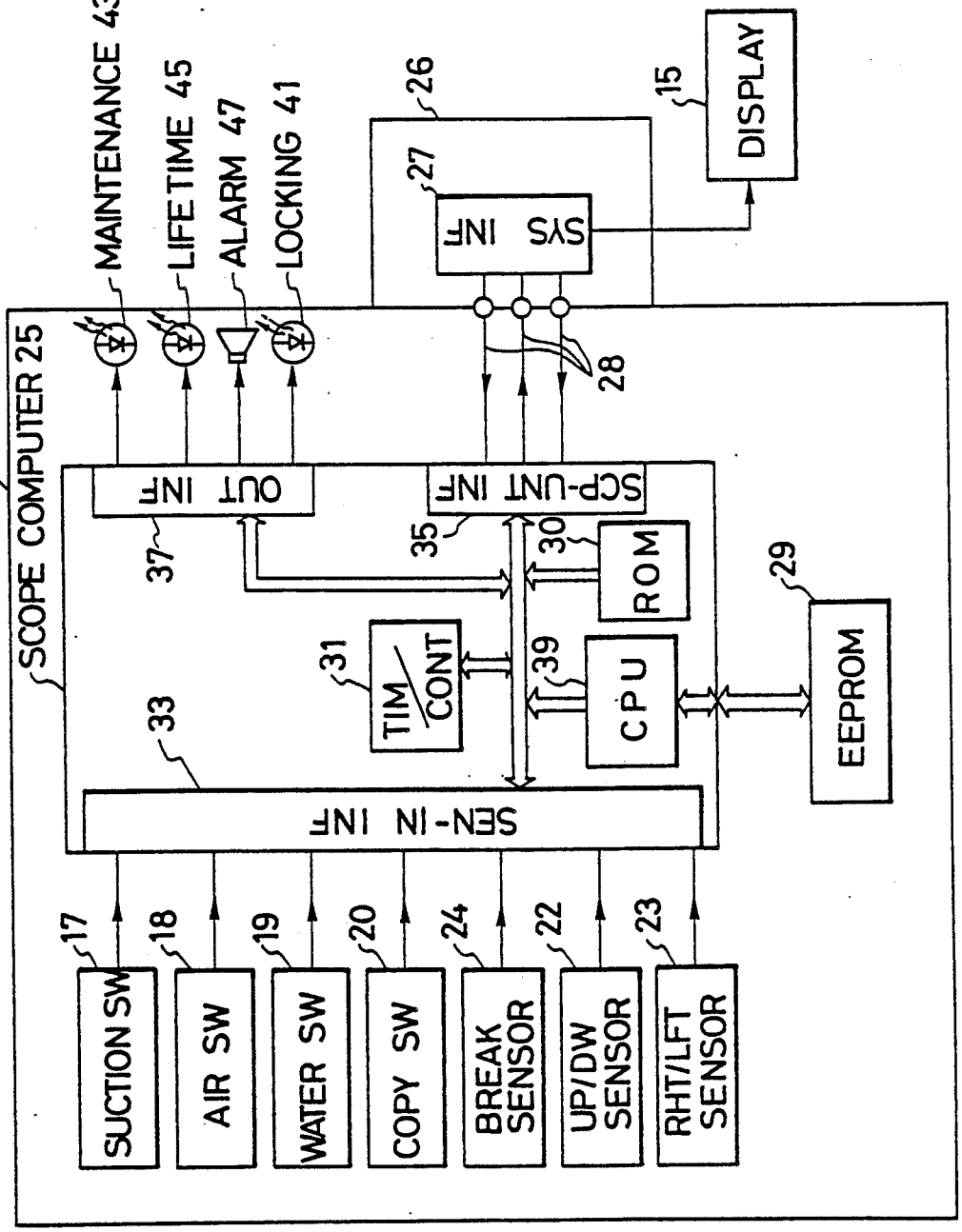
FIG. 4 is a schematic block diagram of an internal circuit arrangement of the electronic endoscope apparatus shown in FIG. 3.

Referring now to FIGS. 3 and 4, an arrangement of an electronic endoscope apparatus according to a first preferred embodiment of the present invention will be described. FIG. 3 is a schematic block diagram of an overall arrangement of the above-described first electronic endoscope apparatus, and FIG. 4 is a schematic block diagram of a major circuit arrangement thereof, i.e., a scope computer 25 and various endoscope members 17 to 24.

In FIG. 3, the first electronic endoscope apparatus is mainly constructed of a scope unit 13 and a main unit 16. The scope unit 13 and main unit 16 include an imaging element 11 such as a CCD (change-coupled device) positioned at a distal end of an electronic scope insertion portion (not shown in detail) and for imaging a body cavity of a biological body (not shown) under medical examination; a video circuit 12 for processing an imaging signal from the imaging element 11 to obtain an endoscope video signal having a proper amplitude; a signal processing circuit 14 for processing the endoscope video signal to produce a television endoscope signal; and a display unit 15 for display an interior image of the biological body under examination thereon.

Furthermore, a system computer 26 is employed in the main unit 16 so as to receive various instruction signals derived from a keyboard 48 and to control the display unit 15 and also to communicate with a scope computer 25 provided within the scope unit 13. Also in the scope unit 13, there are provided an EEPROM (electrically-erasable programmable read-only memory) 29 functioning as a memory; various switches for controlling various endoscope operations, namely a suction switch 17 for controlling or switching the air suction operation, an air switch 18 for controlling an air supply, a water switch 19 for controlling a water supply, a copy switch 20 for controlling a photographing operation; and also an angle operation unit 21 for controlling a curved (angle) unit of the electronic scope along up/down and right/left directions with respect to a longitudinal direction of the electronic scope. In this angle operation unit 21, there are employed three sensors 22, 23 and 24. More specifically, the up/down sensor 22 senses whether or not the angle operation of the curved portion has been performed in the up or down direction. The right/left sensor 23 senses whether or not the angle operation of the curved portion has been effected in the right or left direction. The break sensor 24 senses whether or not the curved condition of the curved portion is held at one of the, above-described angle-operation directions. For instance, the curved portion of the electronic scope is maintained in the up direction. These sensors 22 to 24 and switches 17 to 20 are electrically connected also to the scope computer 25 manufactured by a single IC chip.

As apparent from FIG. 4, a central processing unit 39 employed in the scope computer 25 is connected via a sensor input interface (SEN-IN INF) 33 to the above-described suction switch 17, air supply switch 18, water supply switch 19, copy switch 20 and break sensor 24, up/down sensor 22 and also R/L sensor 23. This CPU 39 reads a predetermined software (will be described later) from ROM (read-only memory) 30 so as to acquire various sensor signals and switching signals via the sensor input interface 33 from the various switches 17 to 20 and various sensors 22, 23 and 24.

Also, a timer/counter (TIM/CONT) 31 is built in the scope computer 25. The function of this timer 31 is to measure an accumulated operation time period of the scope unit 13, whereby use time periods for each endoscopic operation can be measured, and to count use numbers of the respective sensors 22 to 24. To this scope computer 25, a nonvalatile memory, e.g., EEPROM (Electrically-Erasable Programmable Read-only memory) 29 is connected. This EEPROM 29 stores the counted use numbers of the respective sensors and furthermore the accumulated operation time period, which have been measured by the timer/counter 31. The data stored in this EEPROM 39 never disappear even when a power supply (not shown) is turned off.

The CPU 39 is connected via an output interface (OUT INF) 37 to a locking-state display lamp 41 for displaying that the angle operation unit 21 is locked; a periodric maintenance indicating lamp 43 for announcing a necessity of a periodric maintenance; a lifetime warning lamp 45; and a warning buzzer 43 for announcing necessities of periodic maintenance and lifetime respectively. Although not shown in the drawings, lamps and buzzer similar to these lamps 41, 43, 45 and buzzer 47 are provided with the main unit 16. Since the scope computer 25 is connected via a scope unit interface 35, a communication line 28, and a system interface 27 to the system computer 26, the endoscope data are communicated between these computers 25 and 26.

The system computer 26 is connected to the display unit 15 so that various information on the use-history data or the like of the respective members is displayed on the display unit 15 in response to the various signals read from EEPROM 29. Further, this system computer 26 is connected to a keyboard 48 so as to instruct the display unit 15 in such a manner that a fetching signal with respect to the accumulated use time period or the like stored in EEPROM 29 is given from the keyboard 48 to the system and scope computers 25 and 26, and also this accumulated use time period data is displayed on the display unit 15.

Overall Operation of First Electronic Endoscope Apparatus

Referring now to flowcharts shown in FIGS. 5 to 8, an overall operation of the first electronic endoscope apparatus represented in FIGS. 3 and 4 will be described. It should be noted that the following overall operation is mainly executed under the control of the scope computer 25 and also the above-described first and second basic ideas of the present invention are performed.

First, in FIG. 3, when the scope unit 13 is connected to the main unit 16 and the power supply is turned ON, a check is made whether or not a warning flag is set in the scope computer 25 (steps S51 to S54). Since this warning flag is set in EEPROM 29, the value of this warning flag does not change even when the power supply is turned OFF, and therefore the previous value thereof has been stored therein. If one scope unit 13 whose final accumulated time period has passed the allowable use limit time when the power supply was turned ON at the previous endoscope operation, is tried to be used at this present endoscope operation ("YES" at the step S51), the lifetime warning lamp 45 is turned ON at the step S52, the warning buzzer 47 is energized at the next step S53, and thereafter the warning signal is produced from the scope computer 25 to be sent to the system computer 26 employed in the main unit 16 at a step S54. As a result, another lifetime warning lamp and warning buzzer (not shown) employed in the main unit 16 are similarly turned ON. Alternatively, a warning indication may be made on the display unit 15 of the main unit 16. Furthermore, when the scope unit 13 is connected to the main unit 16 and thus the data transfer from the scope computer 25 to the system computer 26 is detected by the system computer 26, the above-described accumulated time data and other necessary data may be read out from EEPROM 29 and displayed on the display unit 16.

To the contrary, when a judgement is made that the accumulated use time period of the electronic scope unit 13 has not yet exceeded over the allowable time limit thereof ("NO" at the step S51), a maintenance flag is then checked at a step S55. Also this maintenance check flag is stored in EEPROM 29 where the previous value of the maintenance check flag has been stored.

If the scope unit 13 whose accumulated use time period has passed a predetermined time period for a periodric maintenance is again attempted to be utilized for the endoscope examination ("YES" at a step S55), the maintenance indicating lamp 43 is turned ON at a step S56 and a turn-ON signal is sent from the scope computer 25 to the scope computer 26 in order to cause another maintenance indicating lamp (not shown) employed in the main unit 16 at a next step S57. Accordingly, the maintenance indicating lamp of the main unit 16 is also turned ON. Alternatively, an indication to require a periodric maintenance may be made on the display unit 15 in the main unit 16.

On the other hand, if confirmation is made that the presently checked accumulated use time period of the electronic scope unit 13 has not yet exceeded over a predetermined periodric maintenance time period ("NO" at the step S55), information with respect to a use history (referred to as "use history data" of this scope unit 13 is transferred from the scope unit 13 to the main unit 16 at a step S58 so as to be stored into RAM 10 employed in the main unit 16.

Operation Switch Sensing Subroutine

Figure 6B:
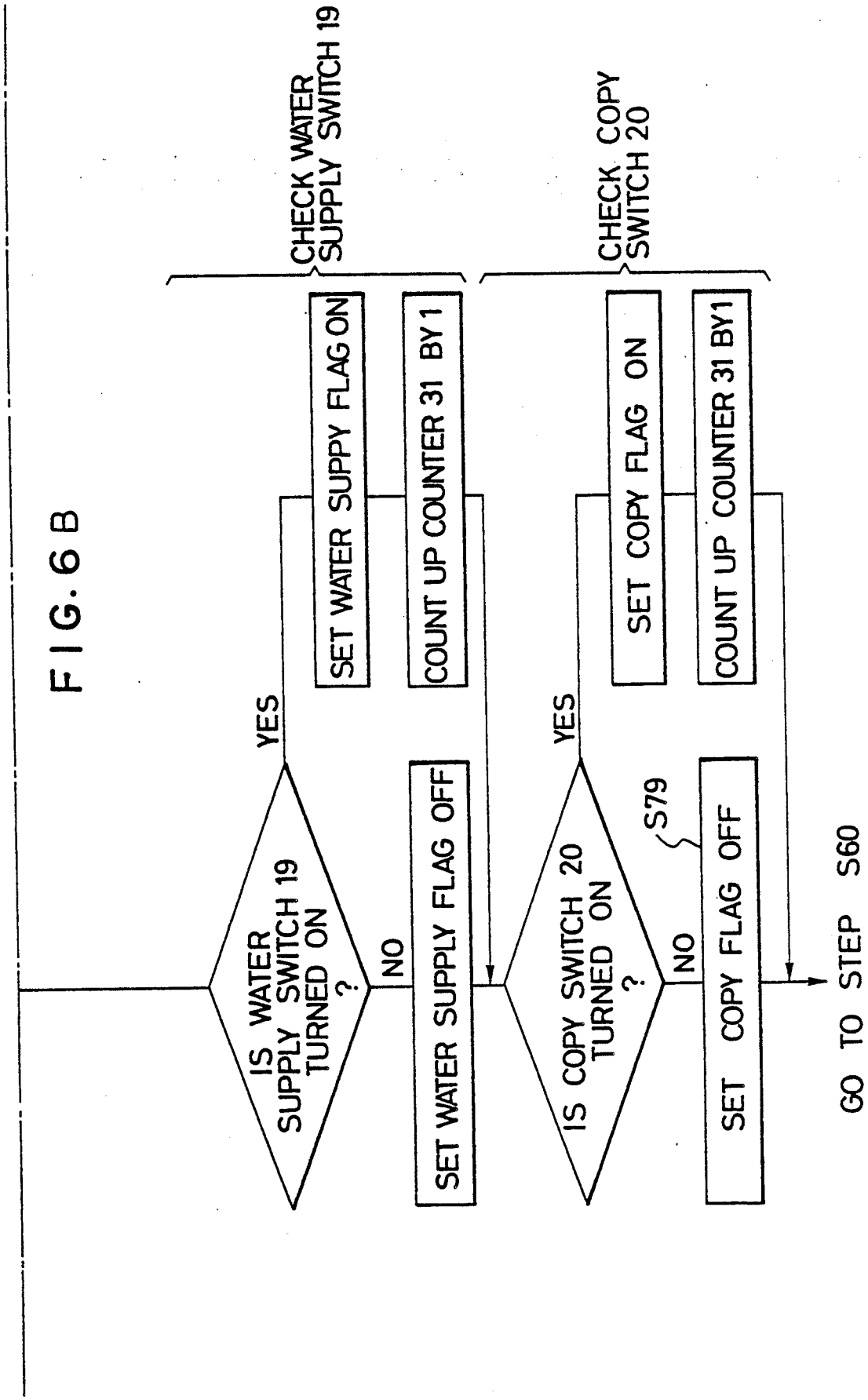

At a next step S59, a subroutine for an operation switch sensing mode is carried out as represented in a flowchart of FIG. 6. In this operation switch subroutine, checks are made whether or not the suction switch 17, air supply switch 18, water supply switch 19, and copy switch 20 are operated, and also operation times of these operation switches are counted by the timer/counter 31.

More specifically, in accordance with this operation switch sensing subroutine, as shown in FIG. 6, when for instance a check is made whether or not the suction switch 17 is turned ON (at a step S71) and this switch is operated, a suction flag used to be utilized for a further process in the system computer 26 is set to "ON" at a step S72, and also an operation number of the suction switch 17 is counted up by 1 in the timer/counter 31 employed in the scope computer 25 at a step S73. If the suction switch 17 is turned OFF at the previous step S71, the suction flag is set to OFF at a step S74.

The similar switch checking process is performed from a step S75 to a step S79 with respect to the operation conditions of the air supply switch 18; water supply switch 19, and copy switch 20 in a predetermined sequence, as illustrated in FIG. 6. No more detailed explanation is made in the specification.

The counted values of these operation numbers for the switches 17 to 20 are stored in EEPROM 29. It should be noted that these counted values may be reset only when these operation switches are substituted by new switches, and these counted values are accumulated every time the same operation switches are utilized for the endoscopic operation.

After the operation state of the copy switch 20 has been checked, the process is advanced to a further step S60 shown in FIG. 5.

Angle Operation Sensing Subroutine

At this step S60, a subroutine for sensing an angle operation is executed as represented in a flowchart shown in FIG. 7.

As shown in FIG. 7, a first check is made to the break sensor 24. If the angle operation unit 21 is under locking state ("YES" at a step S81), then a locking flag is set to "ON" at a step S82, the locking indication lamp 41 is turned ON at a step S83, and the timer/counter 31 is counted up by 1 at a step S84. Conversely, if no angle operation unit 21 is under locking state ("NO" at the step S81), then the locking flag is set to OFF at a step S85 and the locking state indicating lamp 41 is turned OFF at a step S86.

At a next step S85, a check is made whether or not the angle operation unit 21 is operated in an up direction. If YES, then the process is advanced to a step S86 in which the timer/counter 31 is counted up by 1. To the contrary, if NO at the previous step S85, then another check is made whether or not the angle operation unit 21 is operated in a down direction. If YES, then the process is advanced to a step S87 where the timer/counter 31 is counted up by 1. Subsequently, the similar angle operation check is carried out from a step S88 to a step S90 with respect to the right/left sensor 23.

It should be noted that the above-described flag setting operations are omitted, since the various operation states for the up-operation or the like are not required to be utilized in the subsequent process.

Operation Number Checking Subroutine

Figure 8A:
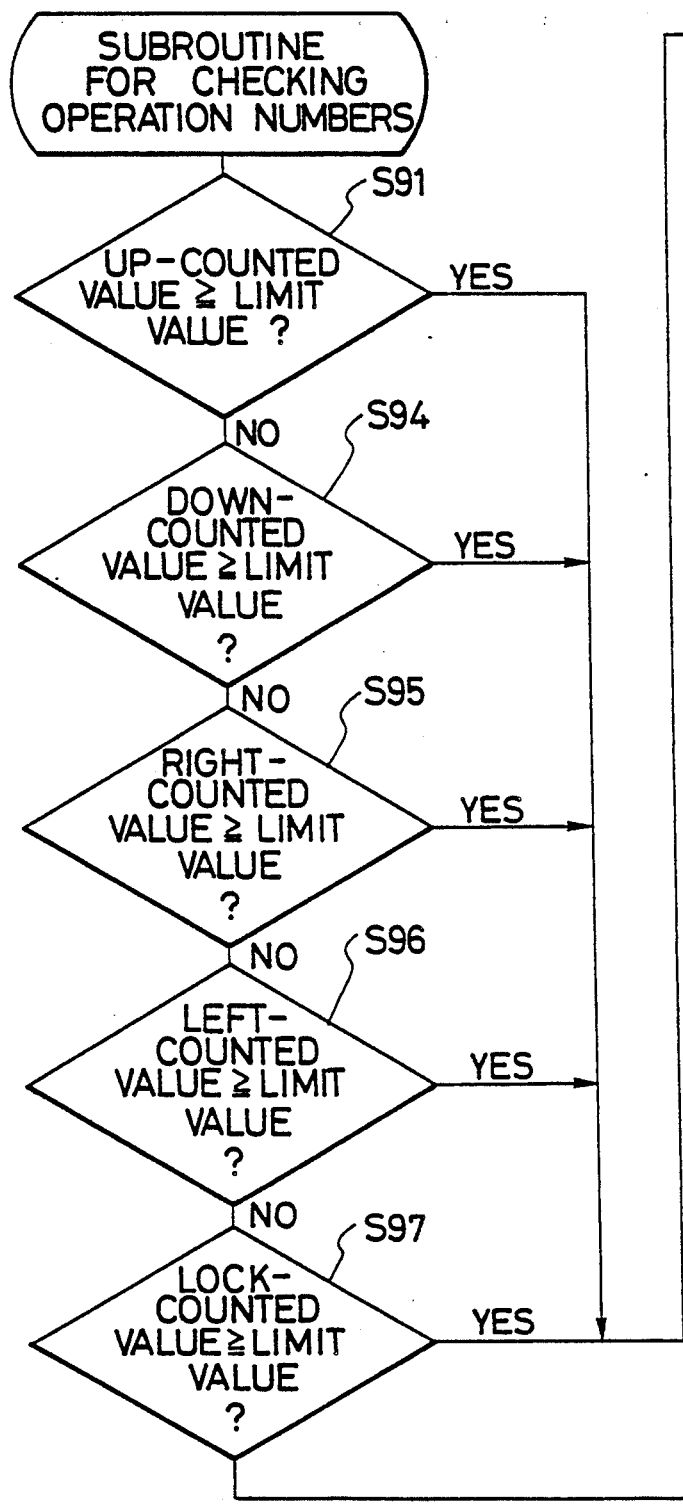
Figure 8B:
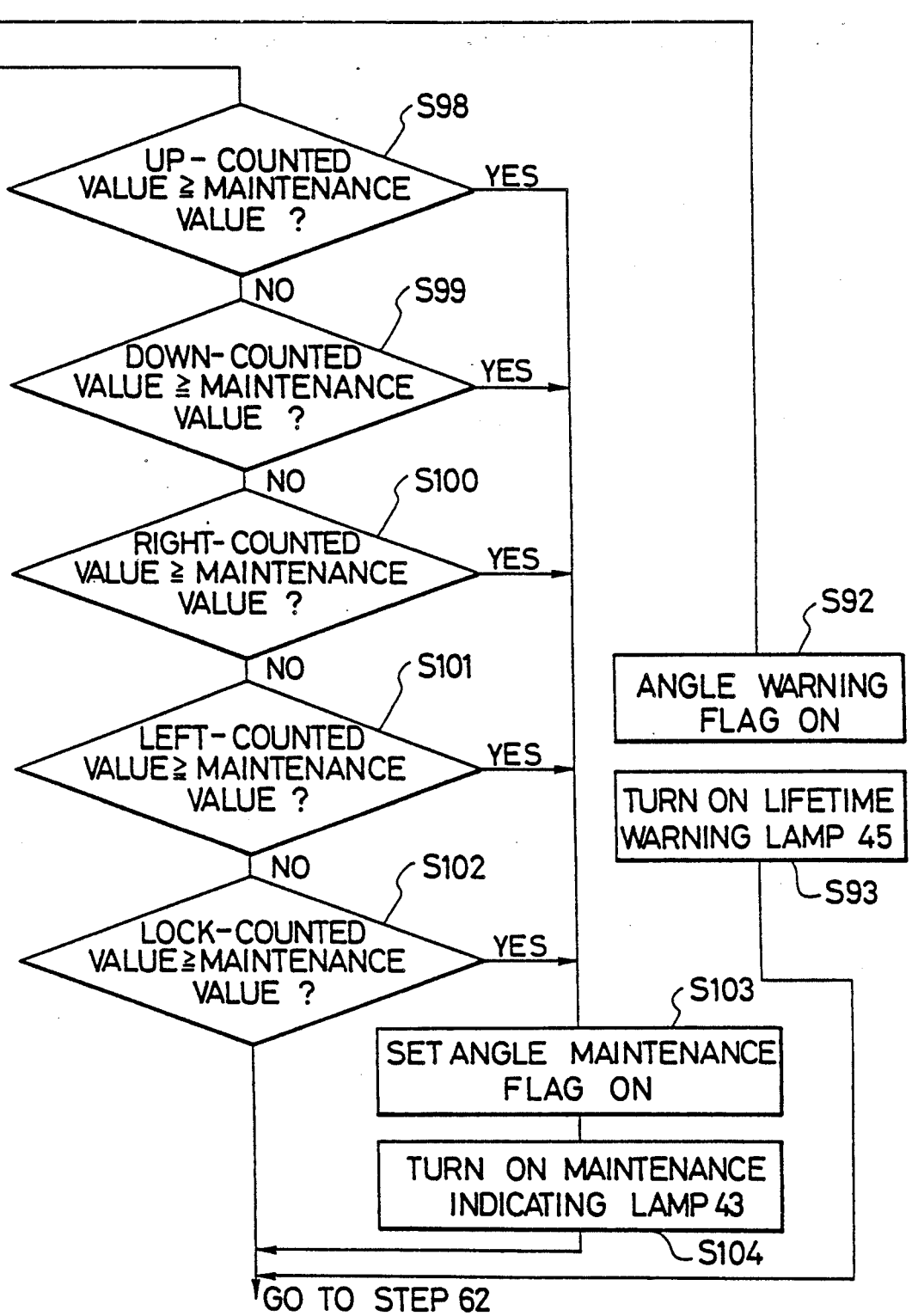

At a subsequent step S61, a subroutine for checking operation numbers of the various switches and angle operations is executed in accordance with a flowchart shown in FIG. 8.

At a first step S91 of the subroutine shown in FIG. 8, a check is made whether or not a counted number (value) of the up counter (i.e., the timer/counter 31 of the scope computer 25) exceeds over a predetermined warning set value, i.e., a limit operation number for manipulating the angle unit 21 in the up direction.

If YES, then a flag for an angle operation warning purpose is set to "ON" at a step S92 and thus the lifetime warning lamp 45 is turned ON at a next step S93. It should be noted that since lifetimes of the angle operations in the respective directions, i.e., UP/DOWN, RIGHT/LEFT are not identical to each other in the angle operation unit 21, the above-described warning set values are inherently preset to the respective angle operation directions. Therefore, the angle operation limit value checkings are independently performed at steps S94 to 97 respectively.

During a next subroutine operation, a maintenance time checking is carried from a step S98 to S102. For instance, if the above-described counted value of the up-counter exceeds over a preset value for a maintenance period, e.g., 10,000 times per six months, then a flag for an angle periodric maintenance is set to "ON" at a step S103. Similarly, 5,000 times/six months are preset for the right/left angle-operation directions, whereas 30,000 times/six months are preset for the operation switches, e.g., the copy switch 20. Furthermore, the periodric maintenance indicating lamp 43 is turned ON at a next step 104. As previously described in detail, both the periodric maintenance warning operation and lifetime warning operation are performed by way of the lamp 43 and buzzer 47 at the beginning of using the electronic scope unit 13. However, since both the warning operations are carried out only by the lamp 43 during the use of the scope unit 13, no anxiety is given to a patient under medical examination.

Thereafter, returning back to a step S62 of the main routine shown in FIG. 5, the OPERATION data communication is carried out between the scope unit 13 and main unit 16. In this step S62, the information on the above-described respective flags which have been set to "ON" at the respective steps, are transferred from to scope unit 13 to the main unit 16. Furthermore, when a demand is made from the main unit 16, the various counted values which have been stored in EEPROM 29 are called and thereafter sent via the system computer 26 to the display unit 15, whereby various use history information can be displayed thereon at a next step S63. As previously stated, both the first and second basic ideas of the present invention have been realized in the first electronic endoscope apparatus shown in FIGS. 3 and 4.

Arrangement of Second Endoscope Assembly

Figure 9:
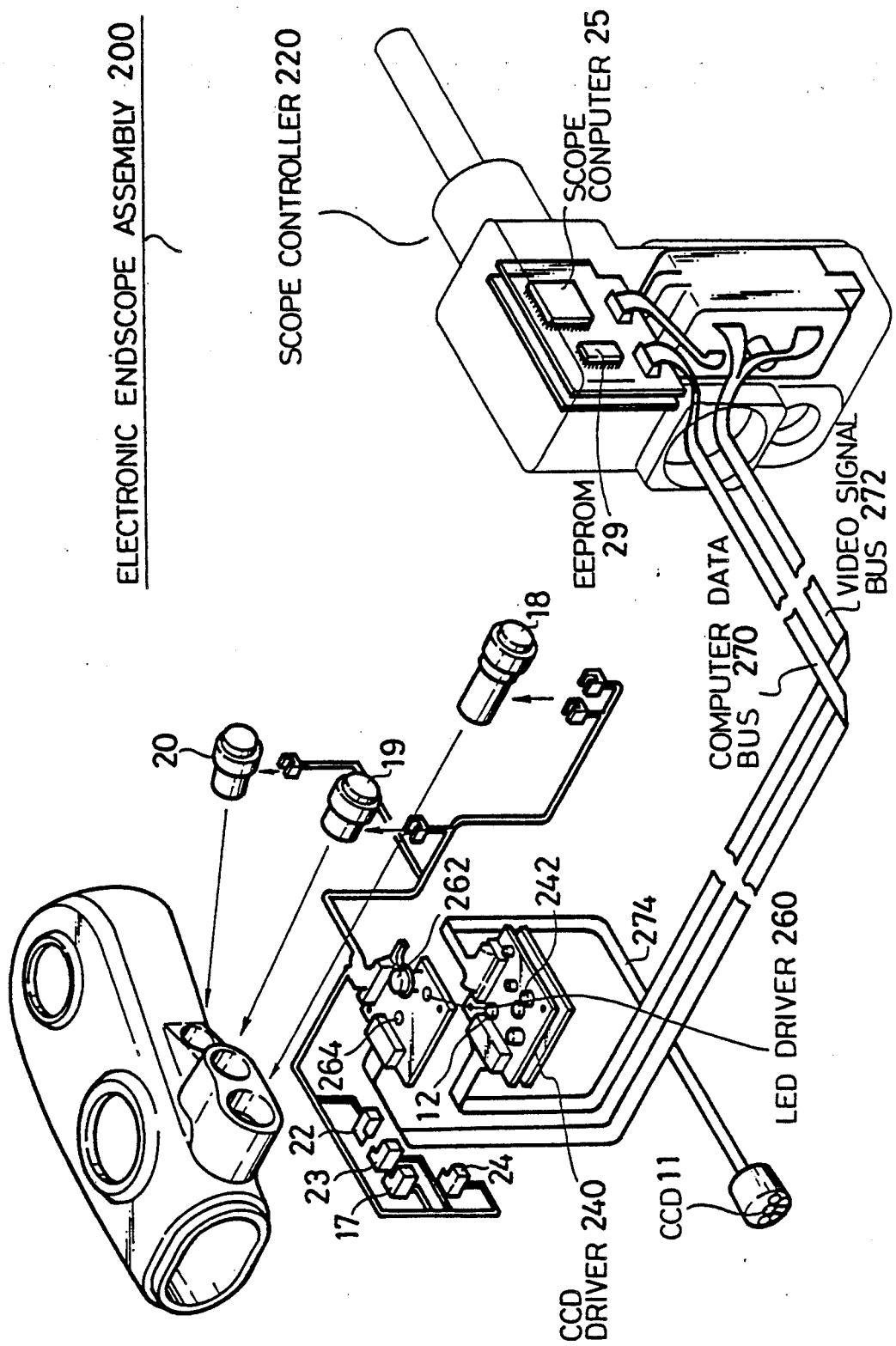

In FIG. 9, there is shown an illustration of an overall arrangement of an electronic endoscope assembly 200 according to a second preferred embodiment of the present invention.

A major feature of this second electronic endoscope unit 200 is to mount EEPROM 29 and a peripheral circuit thereof within this scope assembly 200. As apparent from FIG. 9, this electronic endoscope assembly 200 is mainly constructed of a scope control unit 220, a CCD driver unit 240 and an LED driver unit 260.

Both EEPROM 29 and the scope computer 25 are assembled in the scope control unit 220. A CCD drive circuit 242 and the amplifier 12 are assembled in the CCD driver unit 240. This CCD driver unit 240 is electrically connected via a video signal bus 272 to the scope control unit 25. The CCD drive circuit 242 is connected via a CCD cable 274 to the CCD 11. A relay 262 and an LED drive circuit 264 are assembled in the LED DRIVER unit 260. This LED driver unit 260 is connected to the various operation switches 17 to 20 and 22 to 24, and also connected via a computer data bus 270 to the scope control unit 220.

Since the scope computer 25 and EEPROM 29 are completely assembled within the electronic endoscope assembly 220, use history data which is specific to an electronic endoscope assembly in use can be exclusively stored in EEPROM 29 employed therein. As a result, even when a plurality of endoscope assemblies are simultaneously used during one endoscopic examination, there is no confusion in the stored use history data of these endoscope assemblies.

Modifications

The present invention is not limited to the above-described first and second preferred embodiments, but may be modified, changed, and substituted without departy from the technical scope of the present invention.

In the above-described preferred embodiments, EEPROM 29 was employed as the nonvolatile memory device. Alternatively, EPROM (erasable programmable read-only memory) and ROM (read-only memory) may be employed. Although both the endoscope image of the biological body under medical examination acquired by CCD 11 and the use history data are displayed on the common display unit 15, the use history data may be separately displayed on an additional LCD (liquid crystal display) monitor (not shown) mounted on the scope unit 13.

In the above-described first preferred embodiment, the checking subroutine was carried out from the suction switch 17 to the copy switch 20. However, this switch checking sequence is not limited to the above-described sequence as shown in the flowchart of FIG. 6. Similarly, the angle operation checking sequence is not restricted to that of the subroutine shown in FIG. 7, but may be freely changed.

Moreover, although EEPROM 29 stored only the use numbers of the respective endoscope members and the used time periods thereof in the above-described preferred embodiments, both temperatures and humidity of the insertion portion of the electronic scope unit 13 are detected and may be additionally stored therein.

Based upon these acquired data, a tension lifetime of the angle wire employed in the curved portion of the scope unit 13 may be determined. Also, both temperatures and humidity of the scope unit 13 during the conservation are detected to be stored, so that the conservation conditions thereof.

In the above-described preferred embodiments, both the first and second basic ideas of the present invention were performed. Alternatively, only one of these basic ideas may be effected in these preferred embodiments.

Advantages

As previously described in detail, there are particular advantages of the present invention as follows:

In accordance with the first preferred embodiment, since the use history information such as the use numbers and used time periods are automatically stored into the nonvolatile memory, such an use history information can be precisely recorded without giving the heavy workloads to an endoscope operator. In addition, the comparisions are made between the actually acquired use history data and the preset lifetimes and periodric maintenance time periods, and the indication lamps and buzzer are turned ON when the electronic scope unit reaches a predetermined lifetime and a preset periodric maintenance time period. As a consequence, no such a cumbersome workload to frequently keep a record on the accumulated time and maintenance time period is given to an endoscope operator. Since such a warning is produced before the endoscope operation, or during the endoscope operation, a serious endoscopic failure can be surely prevented, resulting in an improvement of the reliabilities of the electronic endoscope apparatus.

Moreover, when the use history information is fetched from the nonvolatile memory so as to be displayed on the display unit 15, it is very convenience to know the use numbers of the electronic scope unit 13 for a maintenance service. Similarly, when an analysis is made to this fetched use history information in order to correctly and precisely grasp the use conditions of the scope unit 13, a total time required for repairing the scope unit 13 may be saved, and furthermore the analyzed data may be useful for setting both the proper lifetimes and periodric maintenance time periods, and also for improving the performance of the scope unit 13.

In accordance with the second preferred embodiment, there are other particular advantages that since the nonvolatile memory and the peripheral circuits are equipped with the electronic scope assembly and thus each of the use history data is exclusively stored in the respective scope assemblies, there is no confusion of the use history data even when a plurality of scope assemblies are selectively utilized during one endoscope operation. In other words, since use history data is specifically acquired and stored in a specific electronic scope assembly, this specific use history data is only available for this specific scope assembly.

What is claimed is:

1. An electronic endoscope apparatus comprising:
   detector means for detecting use-condition data on an endoscopic operation member;
   detector means for accumulating each of the use-condition data with each other to store the accumulated use-condition data therein as use-history data on the endoscopic operation member; and,
   display means for displaying the use-history data on the endoscopic operation member.

2. An electronic endoscope apparatus as claimed in claim 1, wherein said endoscope operation member includes at least one of an air suction switch, an air supply switch, a water supply switch, a copy switch, and an angle operation sensor for an electronic scope.

3. An electronic endoscope apparatus as claimed in claim 2, wherein said angle operation sensor is constructed of a first sensor for sensing an angle operation of the electronic scope in up/down directions with respect to a longitudinal direction of the electronic scope, a second sensor for sensing the angle operation thereof in right/left directions with respect to said longitudinal direction, and a third sensor for sensing a break condition of the angle operation.

4. An electronic endoscope apparatus as claimed in claim 1, wherein said storage means includes a timer/counter and an EEPROM (electrically-erasable programmable read-only memory), whereby at least one of use numbers and use time periods for the endoscopic operation member are detected as the use-condition data so as to judge whether or not the electronic scope requires one of a periodric maintenance and a replacement by a new electronic scope.

5. An electronic endoscope apparatus comprising:
   detector means for detecting use-condition data on an endoscopic operation member;
   storage means for accumulating each of the use-condition data with each other to store the accumulated use-condition data therein as use-history data on the endoscopic operation member;
   comparator means for comparing the use-history data with use-limit data preset for the endoscopic operation member to derive a comparison result signal; and,
   warning producing means for producing a warning in response to the comparison result signal so as to grasp a use limit condition of the electronic scope.

6. An electronic endoscope apparatus as claimed in claim 5, wherein said endoscope operation member includes at least one of an air suction switch, an air supply switch, a water supply switch, a copy switch, and an angle operation sensor for the electronic scope.

7. An electronic endoscope apparatus as claimed in claim 6, wherein said angle operation sensor is constructed of a first sensor for sensing an angle operation of the electronic scope in up/down directions with respect to a longitudinal direction of the electronic scope, a second sensor for sensing the angle operation thereof in right/left directions with respect to said longitudinal direction, and a third sensor for sensing a break condition of the angle operation.

8. An electronic endoscope apparatus as claimed in claim 5, wherein said storage means includes a timer/counter and an EEPROM (electrically-erasable programmable read-only memory), whereby at least one of use numbers and use time periods for the endoscopic operation member are detected as the use-condition data so as to judge whether or not the electronic scope requires one of a periodric maintenance and a replacement by a new electronic scope.

9. An electronic endoscope apparatus as claimed in claim 5, wherein said comparator means includes:
   a read-only memory for previously storing the use-limit data preset for the endoscopic operation member; and,
   a central processing unit for processing the use-history data read out from the storage means based upon the use-limit data so as to obtain the comparison result signal.

10. An electronic endoscope apparatus as claimed in claim 5, wherein said warning producing means includes at least one of a locking-condition indicating lamp, a maintenance indicating lamp, a lifetime indicating lamp, and a warning lamp.

11. An electronic endoscope apparatus comprising:
an electronic scope having an image sensor at a distal end thereof and an angle operation portion adjacent to the image sensor;
a scope unit coupled with the electronic scope, including an endoscopic operation switch mechanically connected to the electronic scope, a scope computer for processing a switch operation signal derived from the endoscopic operation switch so as to obtain first use-history data on the operation switch, and a memory device for temporarily storing the first use-history data therein; and,
a main unit including a signal processor for processing an image signal derived from the image sensor so as to produce an endoscopic image signal of a biological body under medical examination, a system computer for fetching the use-history data on the operation switch from the memory device via the scope computer, and a display unit for selectively displaying an endoscopic image of the biological body in response to the endoscopic image signal and use-history information in response to the fetched used-history data.

12. An electronic endoscope apparatus as claimed in claim 11, wherein said memory device employed in the scope unit further stores use-limit data on the operation switch, said scope computer compares the first use-history data with the use-limit data so as to derive a comparison result signal, and a use-condition indicator for the electronic scope is further employed in order to indicate a use limit condition of the electronic scope in response to the comparison result signal.

13. An electronic endoscope apparatus as claimed in claim 11, further comprising:
a sensor mechanically connected to the angle operation portion of the electronic scope, for sensing an angle-operation condition thereof to produce an angle operation signal, whereby said scope computer employed in the scope unit processes the angle operation signal so as to obtain second use-history data on the angle operation portion.

14. An electronic endoscope apparatus as claimed in claim 13, wherein said memory device employed in the scope unit further stores use-limit data on the operation switch and said second use-history data on the angle operation portion, said scope computer compares at least one of said first and second use-history data with the use-limit data so as to derive a comparison result signal, and a use-condition indicator for the electronic scope is further employed in order to indicate a use limit condition of the electronic scope in response to the comparison result signal.

15. An electronic endoscope apparatus as claimed in claim 11, wherein said endoscope operation member includes at least one of an air suction switch, an air supply switch, a water supply switch, a copy switch, and an angle operation sensor for the electronic scope.

16. An electronic endoscope apparatus as claimed in claim 11, wherein said angle operation sensor is constructed of a first sensor for sensing an angle operation of the electronic scope in up/down directions with respect to a longitudinal direction of the electronic scope, a second sensor for sensing the angle operation thereof in right./left directions with respect to said longitudinal direction, and a third sensor for sensing a break condition of the angle operation.

17. An electronic endoscope apparatus as claimed in claim 11, wherein said image sensor is a charge-coupled device, and said memory device is an EEPROM (electrically-erasable programmable read-only memory).

18. An electronic endoscope assembly comprising:
an electronic scope having an image sensor at one end thereof and an angle operation portion adjacent to the image sensor;
an image driver unit for driving the image sensor to produce an endoscopic image signal of a biological body under medical examination; and,
a scope control unit connected to the other end of the electronic scope, including a scope computer for processing a switch operation signal derived from an endoscope operation switch mechanically connected to the electronic scope so as to obtain first use-history data on the operation switch, and a memory device for temporarily storing the first use-history data for a use-history condition displaying purpose.

19. An electronic endoscope assembly as claimed in claim 18, wherein said memory device employed in said scope control unit further stores use-limit data on the operation switch, said scope computer compares the first use-history data with the use-limit data so as to derive a comparison result signal for a use-limit condition indicating purpose.

20. An electronic endoscope assembly as claimed in claim 18, wherein said scope computer further processes an angle-operation condition of said angle operation portion so as to obtain second use-history data on the angle operation portion.

* * * * *